US012678572B2

(12) United States Patent
Hsu et al.

(10) Patent No.: US 12,678,572 B2
(45) Date of Patent: Jul. 14, 2026

(54) METHOD FOR ESTIMATING INHALE DOSE OF A PERSON

(71) Applicant: MICROBASE TECHNOLOGY CORP., Taoyuan City (TW)

(72) Inventors: Yu-Chung Hsu, Taoyuan City (TW);
Chien-Hua Lin, Taoyuan City (TW);
Hsin-Hua Tseng, Taoyuan City (TW);
Yi-Shou Chang, Taoyuan City (TW);
Jo-Ling Wu, Taoyuan City (TW);
Hui-Ling Lin, Taoyuan City (TW)

(73) Assignee: MICROBASE TECHNOLOGY CORP., Taoyuan City (TW)

( * ) Notice: Subject to any disclaimer, the term of this patent is extended or adjusted under 35 U.S.C. 154(b) by 831 days.

(21) Appl. No.: 17/923,920

(22) PCT Filed: May 8, 2021

(86) PCT No.: PCT/CN2021/092347
§ 371 (c)(1),
(2) Date: Nov. 8, 2022

(87) PCT Pub. No.: WO2021/223753
PCT Pub. Date: Nov. 11, 2021

(65) Prior Publication Data
US 2023/0166058 A1     Jun. 1, 2023

Related U.S. Application Data

(60) Provisional application No. 63/021,688, filed on May 8, 2020.

(51) Int. Cl.
*A61M 15/00*     (2006.01)
*A61M 11/00*     (2006.01)
(Continued)

(52) U.S. Cl.
CPC ........ *A61M 15/0065* (2013.01); *G16H 20/13* (2018.01); *A61M 11/005* (2013.01);
(Continued)

(58) Field of Classification Search
CPC ................ A61M 15/00; A61M 15/001; A61M 15/0021; A61M 15/0065; A61M 15/0085;
(Continued)

(56) References Cited

U.S. PATENT DOCUMENTS 5,887,586 A * 3/1999 Dahlback .......... A61M 15/0065
                                                128/204.22
6,273,088 B1 8/2001 Hillsman
(Continued)

FOREIGN PATENT DOCUMENTS

CN     107820433 A     3/2018
CN     108261593 A     7/2018
(Continued)

OTHER PUBLICATIONS

International Search Report for PCT/CN2021/092347.

*Primary Examiner* — Joseph D. Boecker

(57)     ABSTRACT

A method for estimating an inhale dose when a drug is delivered to a person using an inhaler is disclosed. A predicted inhale dose (PID) of the drug is estimated based on at least one first-type parameter and at least one second-type parameter. The first-type parameter is related to a breath pattern of the person, and the second-type parameter is related to the inhaler.

15 Claims, 8 Drawing Sheets

(51) Int. Cl.

| | | |
|---|---|---|
| *A61M 16/00* | (2006.01) | |
| *A61M 16/08* | (2006.01) | |
| *G16H 20/13* | (2018.01) | |

(52) U.S. Cl.

CPC ..... *A61M 15/0021* (2014.02); *A61M 15/0085* (2013.01); *A61M 15/009* (2013.01); *A61M 2016/0015* (2013.01); *A61M 2016/0027* (2013.01); *A61M 2016/003* (2013.01); *A61M 16/0833* (2014.02); *A61M 2205/7518* (2013.01); *A61M 2209/02* (2013.01); *A61M 2230/40* (2013.01)

(58) Field of Classification Search

CPC .... A61M 11/00; A61M 11/005; A61M 11/06; A61M 2016/0015; A61M 2016/0027; A61M 2016/003; A61M 2016/0033; A61M 2016/0036; A61M 2209/02; A61B 5/087; A61B 5/4839; G16H 20/13; A24F 40/50; A24F 40/51; A24F 40/53; A24F 40/57

See application file for complete search history.

(56) References Cited

U.S. PATENT DOCUMENTS

| | | | | |
|---|---|---|---|---|
| 2005/0087189 A1* | 4/2005 | Crockford | ............. | A61M 11/06 |
| | | | | 128/203.15 |
| 2005/0166913 A1* | 8/2005 | Sexton | ............. | A61M 15/0065 |
| | | | | 128/200.14 |
| 2014/0339323 A1* | 11/2014 | Bentvelsen | ....... | A61M 15/0085 |
| | | | | 239/11 |
| 2015/0273165 A1* | 10/2015 | Hadash | ............... | A61M 16/202 |
| | | | | 128/203.14 |
| 2016/0157524 A1* | 6/2016 | Bowen | .................... | A24F 40/42 |
| 2017/0079557 A1* | 3/2017 | Lauk | ........................ | A61B 5/74 |
| 2020/0023148 A1 | 1/2020 | Weitzel et al. | | |

FOREIGN PATENT DOCUMENTS

| | | | | | |
|---|---|---|---|---|---|
| EP | 2085105 A1 | 8/2009 | | | |
| GB | 2556016 A | 5/2018 | | | |
| TW | 201513902 A | 4/2015 | | | |
| WO | 9522365 A1 | 8/1995 | | | |
| WO | 2018144964 A1 | 8/2018 | | | |
| WO | WO-2020141999 A1 * | 7/2020 | ........... | A61B 5/7264 |

* cited by examiner

12

12

METHOD FOR ESTIMATING INHALE DOSE OF A PERSON

CROSS-REFERENCE TO RELATED APPLICATION

This application is the US national phase of international application No. PCT/CN2021/092347 filed on May 8, 2021, which claims priority to U.S. provisional patent application No. 63/021,688 filed on May 8, 2020. The contents of the above applications are incorporated herein by reference in their entirety.

BACKGROUND

Technical Field

The disclosure is related to a method for estimating an inhale dose of a patient and, in particular, to a method for estimating the inhale dose according to different type of parameters.

Related Art

An inhaler is a medical device used for delivering drugs through a person's breathing. This allows drugs to be delivered to and absorbed in the lungs, which provides the ability for targeted medical treatment to this specific region of the body, as well as a reduction in the side effects of oral medications. There are a wide variety of inhalers, such as meter-dosed inhalers, dry powder inhalers, and nebulizers.

For example, a nebulizer is used to administer medication in the form of a mist inhaled into the lungs for the treatment of asthma, cystic fibrosis, chronic obstructive pulmonary disease (COPD) and other respiratory diseases or disorders. They break up solutions and suspensions into small aerosol droplets, a mixture of gas and solid or liquid particles, that are inhaled from a patient port.

The actual amount of the drug delivered through an inhaler into the respiratory tract of a person may be quite different from the amount consumed at the aerosol source. For example, the amount of the drug delivered in the form of aerosol droplets may be affected by different breathing patterns of different persons. To treat respiratory diseases through inhalers more effectively, it is crucial to estimate the inhale dose of the drug more accurately considering different parameters.

SUMMARY

A method for estimating an inhale dose when a drug is delivered to a person using an inhaler is disclosed. A predicted inhale dose (PID) of the drug is estimated based on at least one first-type parameter and at least one second-type parameter. The first-type parameter is related to a breath pattern of the person, and the second-type parameter is related to the inhaler.

In one embodiment, the first-type parameter may include an inspiratory time of the person or an expiratory time of the person. The second-type parameter may include a drug deposit in an inlet path of the inhaler or a drug reserve in an outlet path of the inhaler. The predicted inhale dose may be estimated according to the following formula:

$$PID=(TD-RC)*(I/(E+I))-DP+RP$$

wherein TD is the total drug amount in an aerosol generator of the inhaler, RC is the drug residue amount in the aerosol generator, I is an inspiratory time of the person, E is an expiratory time of the person, DP is a drug deposit in an inlet path of the inhaler, and RP is a drug reserve in an outlet path of the inhaler.

In one embodiment, the first-type parameter may be obtained by measuring the breath pattern of the person, and the second-type parameter may be obtained from a look-up table according to the type of the inhaler.

An apparatus for estimating an inhale dose when a drug is delivered to a person using an inhaler is also disclosed. The apparatus includes a processor and a memory. The memory stores instructions for the processor to execute to perform the steps of obtaining a first-type parameter related to a breath pattern of the person, obtaining a second-type parameter related to the inhaler, and estimating a predicted inhale dose of the drug based on the first-type parameter and the second-type parameter. A non-transitory storage medium with instructions stored thereon for estimating an inhale dose when a drug is delivered to a person using an inhaler is also disclosed.

When delivering a drug to a person using an inhaler, a person measures a breath pattern of the person, and input information related to the type of an inhaler. An inhale dose is determined according to a predicted inhale dose of the drug, wherein the predicted inhale dose of the drug is estimated based on a first-type parameter related to a breath pattern of the person and the second-type parameter related to the inhaler.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE DISCLOSURE

System Overview

Figure 1:
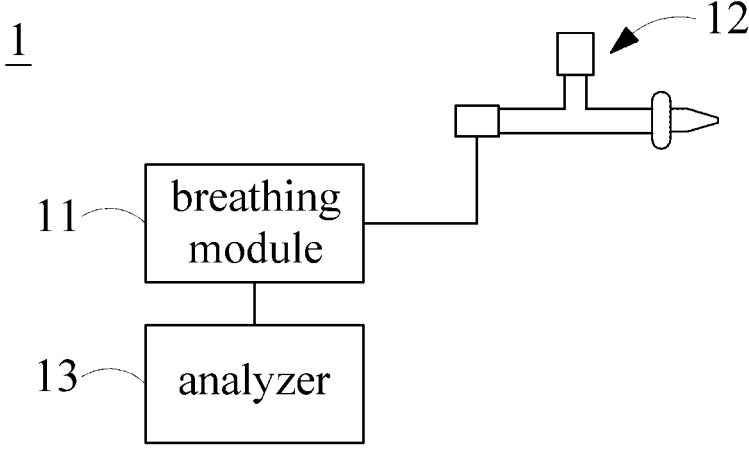
FIG. 1 is a schematic diagram showing the system for estimating the inhale dose of a person according to an embodiment of the disclosure.

Referring to FIG. 1, the system 1 for estimating the inhale dose of a person according to an embodiment includes a breathing module 11, an inhaler 12 and an analyzer 13. The breathing module 11 may be a pressure sensor or flow sensor used to measure the breath pattern of a person, such as the tidal volume (Vt), the inspiratory time (I) and the expiratory time (E) of the person. The breathing module 11 could be disposed within a flow circuit.

Figure 2A:
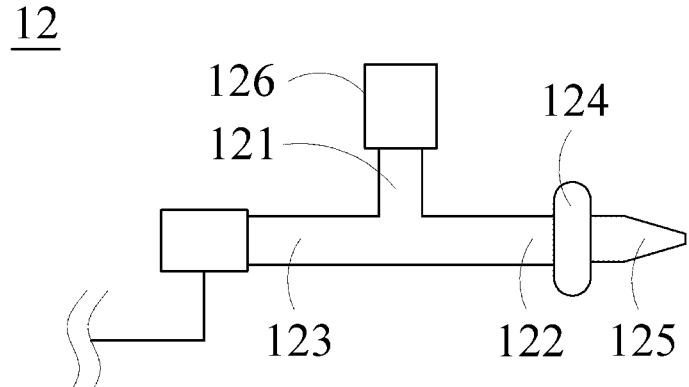
FIG. 2A is a schematic diagram showing the inhaler of the system shown in FIG. 1.
Figure 2B:
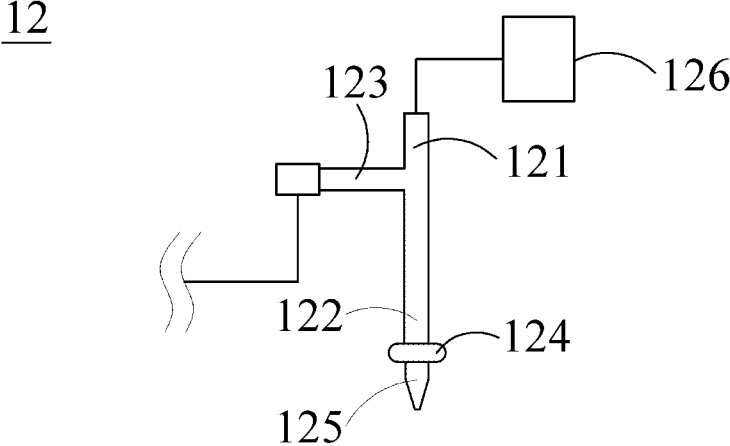
FIG. 2B is a schematic diagram showing another inhaler that may be used in the system shown in FIG. 1.

Referring to FIG. 2A, the inhaler 12 includes a 3-way tube including an aerosol inlet 121, an inlet path 122, an outlet path 123, a filter 124 and a patient port 125. The aerosol inlet 121 may be detachably attached with an aerosol source, such as an aerosol generator 126 for generating aerosol droplets into the inhaler 12. The aerosol inlet 121 may also be detachably attached with the outlet of a nebulizer generating aerosol droplets. Other aerosol sources, such as a metered dose inhaler or a jet nebulizer, may be attached at the aerosol inlet 121.

The filter 124, such as a HEPA filter or a breathing circuit bacterial filter (VF-2160) et al. may be detachably attached between the inlet path 122 and the patient port 125 for filtering out the aerosol droplets within the airflow flowing to and from the patient port 125. The amount of the drug deposited in the filter 124 represents the actual dose of the drug inhaled by the person when breathing through the patient port.

The patient port 125 may be, for example, a mouthpiece, a mask, a respiratory cannula, or any other device that delivers the aerosol droplets into a patient's respiratory tract. When the filter 124 is detached from the inlet path 122, the patient port 125 may be attached to the inlet path 122 without the filter 124 being disposed in between. That is, a patient may inhale his or her drug in the form of aerosol droplets using the inhaler 12 directly without the drug being filtered out by the filter 124.

The aerosol generator 126 may be a portable nebulizer with a container for containing the drug and a vibration module to convert the drug in the container into tiny droplets for respiratory treatment. The aerosol generator 126 may be attached to the aerosol inlet 121 directly or through other means such as a tube.

The configuration of the inhaler 12 may be changed in view of practical applications. For example, as shown in FIG. (b), the inlet path 122 and the outlet path 123 may not be in a straight line but are perpendicular to each other. The aerosol generator 126 is a nebulizer which is fluidly connected with the aerosol inlet 121 with a tube. Persons having ordinary skills in the art may use different types of aerosol generators with different configurations.

The analyzer 13 may be a general-purpose computer or a device with a chip having computational capabilities such as CPU or MCU installed with software for estimating the inhale dose. The analyzer 13 may receive from the breathing module 11 the measurement result of the breath pattern of the person and estimate the inhale dose based on the breath pattern and other parameters. For example, the analyzer 13 may receive the data through wired transmission (ex: USB cable) or wireless transmission (ex: BLE or Wi-fi). After receiving the data from the breathing module 11, the analyzer 13 may display the data on a display using a graphical user interface so that the operator can view the breath pattern of the person in real time. The analyzer 13 may also receive the input of the operator via the graphical user interface, such as the type of the inhaler 12.

Example 1

Figure 3:
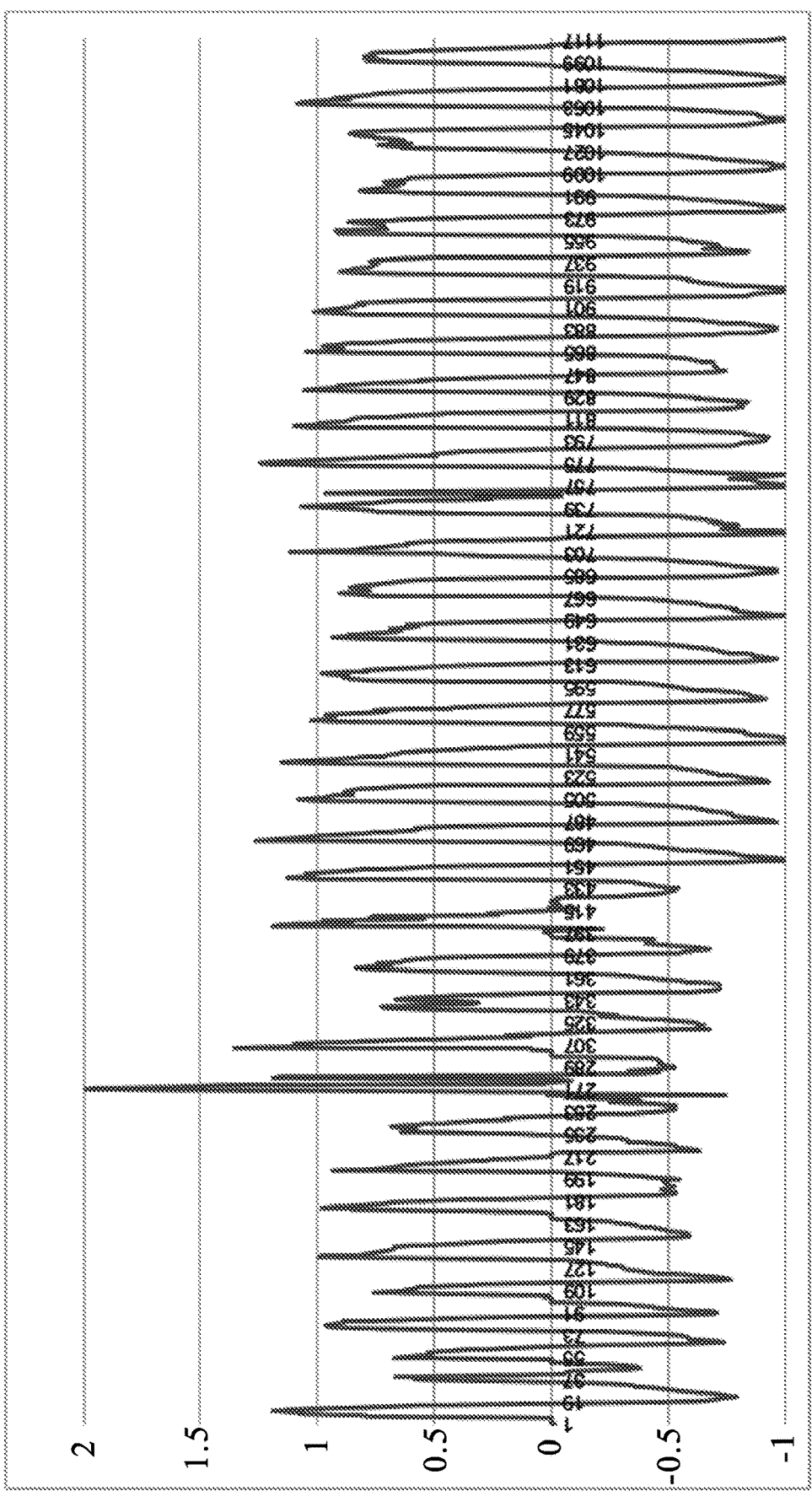
FIG. 3 is a line chart showing an example of the record data of a measured breathing pattern.

FIG. 3 shows an example of the breathing pattern measured by the breathing module 11. A person A breathes using Microbase POCKETAIR®-T3, spray rate 0.55 ml/min to aerosol Salbutamol (5 mg/2.5 ml) by the patient port 125.

The analyzer 13 estimates a predict inhale dose (PID) according to the following formula (1):

$$PID=(TD-RC)*(I/(E+I))-DP+RP \qquad (1)$$

wherein TD is the total drug amount, RC is the drug residue amount in the aerosol generator 126, I is the inspiratory time, E is the expiratory time, DP is the parameter of drug depositing in the inhaler 12, and RP is the parameter of drug reserving in the inhaler 12.

Among the parameters above, TD and RC may be obtained by the input of an operator after examining the aerosol generator 126 attached to the aerosol inlet 121. I and E may be obtained from the breathing module 11. DP and RP are related to the type of the inhaler 12 and can be obtained from a look-up table stored in the memory of the analyzer 13 after the operator inputs the inhaler type. The analyzer 13 selects the apparatus parameter based on the type of the inhaler 12 input by the operator and the breathing parameters output by the breathing module 11. Below is one example of the look-up table:

| | DP | RP |
|---|---|---|
| Inhaler 1 | 1.3% | 9.2% |
| Inhaler 2 | 5.6% | 5.4% |
| Inhaler 3 | 11% | 2.6% |

The operations will be described hereinbelow. After the system 1 is set up, the operator first inputs the type of the inhaler 12 and the total aerosol drug from the aerosol generator 126. The analyzer 13 obtains the parameters DP and RP from a lookup table according to the inhaler type input by the operator. Then, the operator asks the person A to start using the patient port 125 of the inhaler 12 to breath. The breathing module 11 then measures the breath pattern of the person A, including the inspiratory time I and the expiratory time E, and outputs I and E to the analyzer 13. FIG. 3 is the breath pattern in the form of a wave format. After a predetermined period, the operator asks the person A to stop breathing using the patient port 125 and inputs the residue amount in the aerosol generator 126 to the analyzer 13. The analyzer 13 then calculates the PID according to formula (1).

In other case, specific parameters DP and RP may be pre-set in the analyzer 13 for a specific inhaler 12. The operator does not need to input the inhaler type, but only needs to measure the breath pattern for the analyzer 13 to calculate the PID for patient. The analyzer 13 may also be stored with a default residue amount. The operator does not need to input the residue amount in the aerosol generator 126, either.

Figure 4:
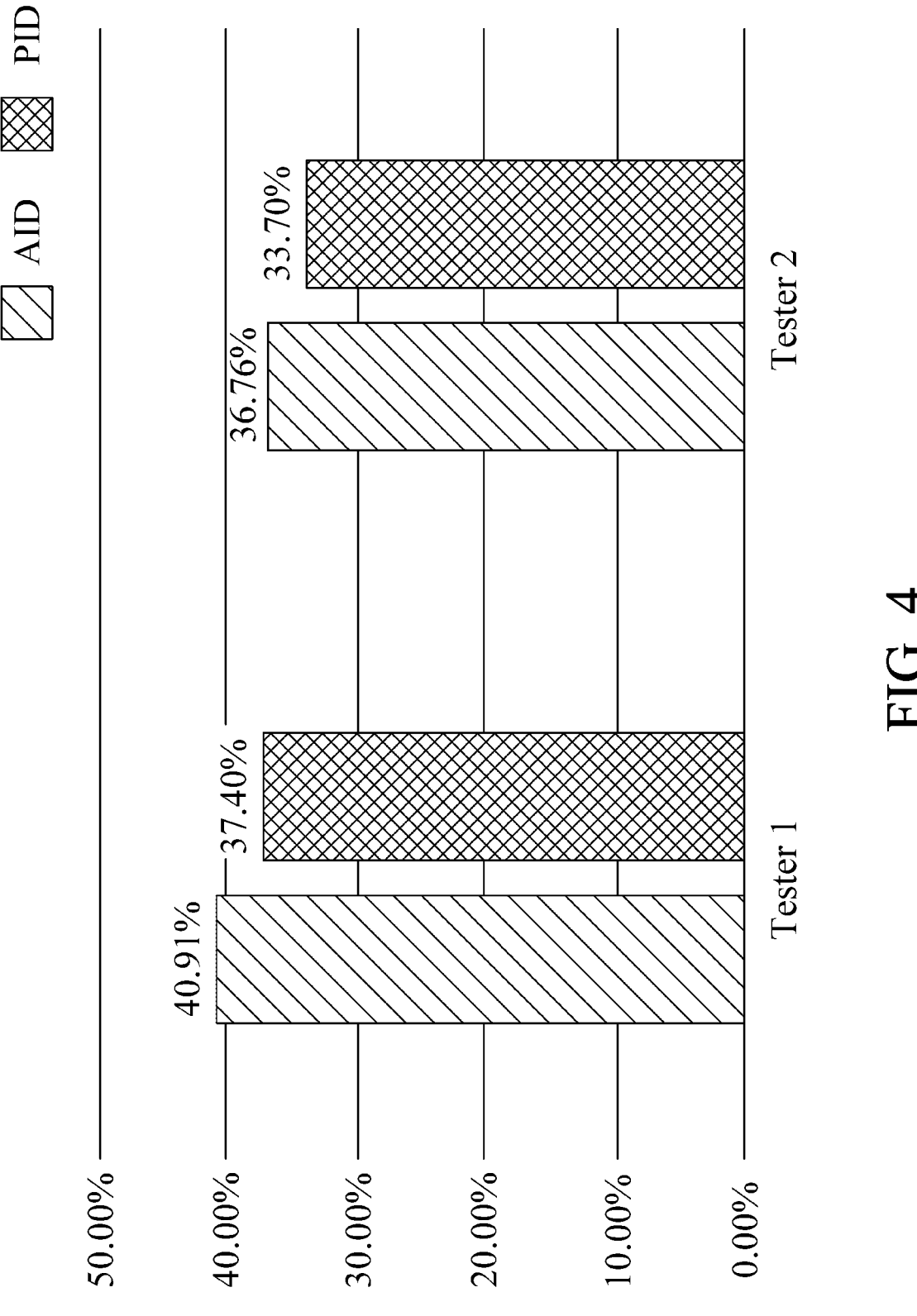
FIG. 4 is a bar chart showing the comparisons of the predicted inhale dose (PID) and the actual inhale dose (AID) of two tests for two different persons.

The operator then detaches the filter 124 from the inhaler 12 and examines the amount of the drug deposited at the filter 124 to obtain the actual inhale dose ("AID") of the person A. FIG. 4 shows the comparisons of the PIDs and the AIDs of two tests for two different persons. In FIG. 4, the tester 1 is a female, the tester 2 is a male. The PID for female tester 1 is 37.40% of the drug aerosolized by the aerosol generator, and the PID for the male tester 2 is 33.70%. As shown in FIG. 4, regardless of the gender, both PIDs are close to the corresponding AIDs, which are 40.91% and 36.76%, respectively.

Figure 5:
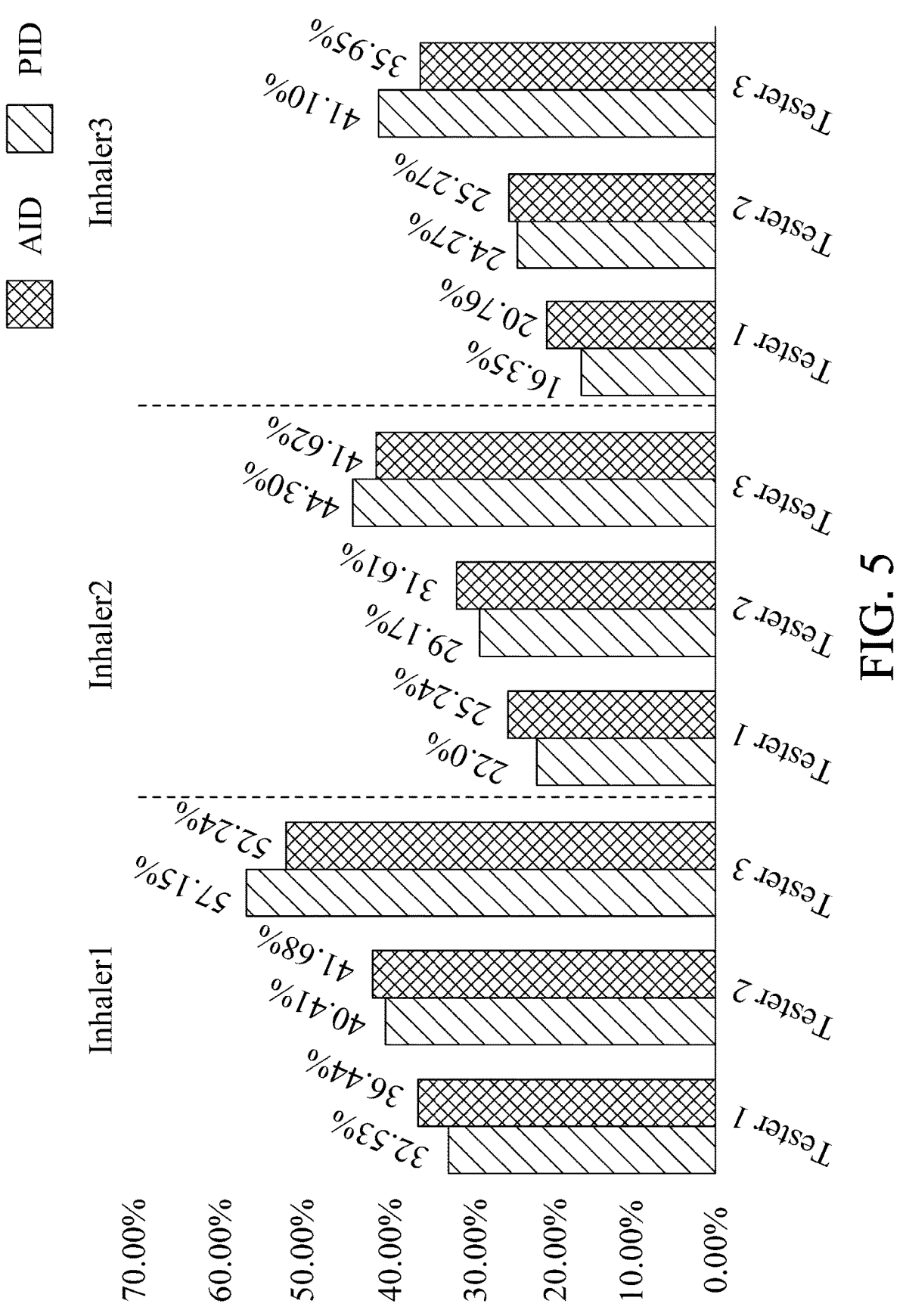
FIG. 5 is a bar chart showing another comparison of the PIDs and the AIDs of three testers using three different inhalers.

FIG. 5 shows another comparison of the PIDs and the AIDs of different testers (Tester 1, Tester 2, Tester 3) using different inhalers (Inhaler 1, Inhaler 2, Inhaler 3). As shown in FIG. 5, although the AIDs using different inhalers are quite different, the PIDs are still close to the AIDs for different inhalers since different characteristics of different inhalers are considered by incorporating the second-type parameter when estimating the PIDs. Therefore, more accurate PIDs can be obtained.

Example 2

Figure 6:
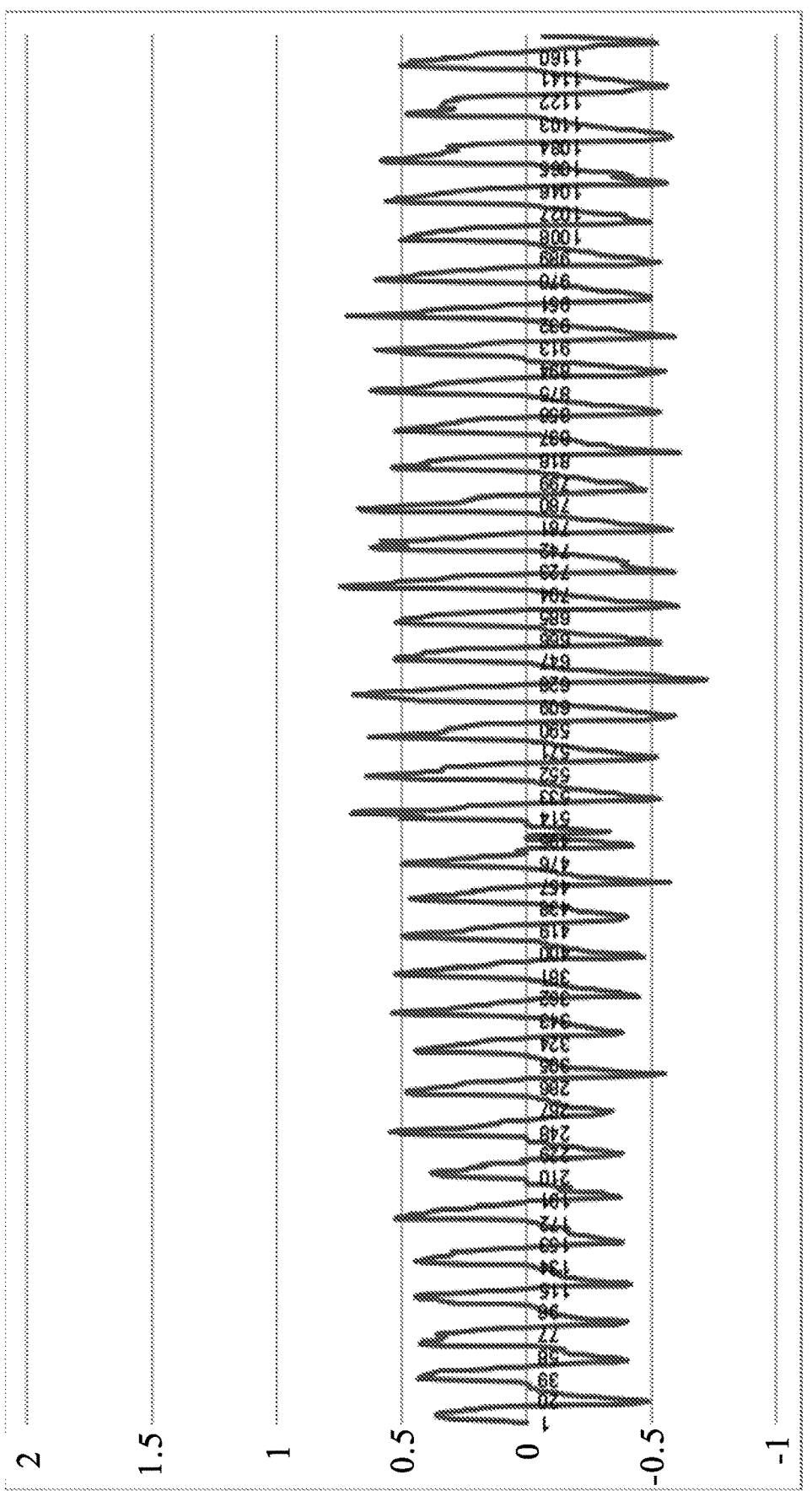
FIG. 6 is a line chart showing another example of the record data of a measured breathing pattern.

FIG. 6 shows another example of the breathing pattern measured by the breathing module 11. A person B breathes using another nebulizer, spray rate 0.3 ml/min to aerosol Salbutamol (5 mg/2.5 ml) by the patient port 125. The analyzer 13 estimates a PID according to the formula (1) above.

Figure 7:
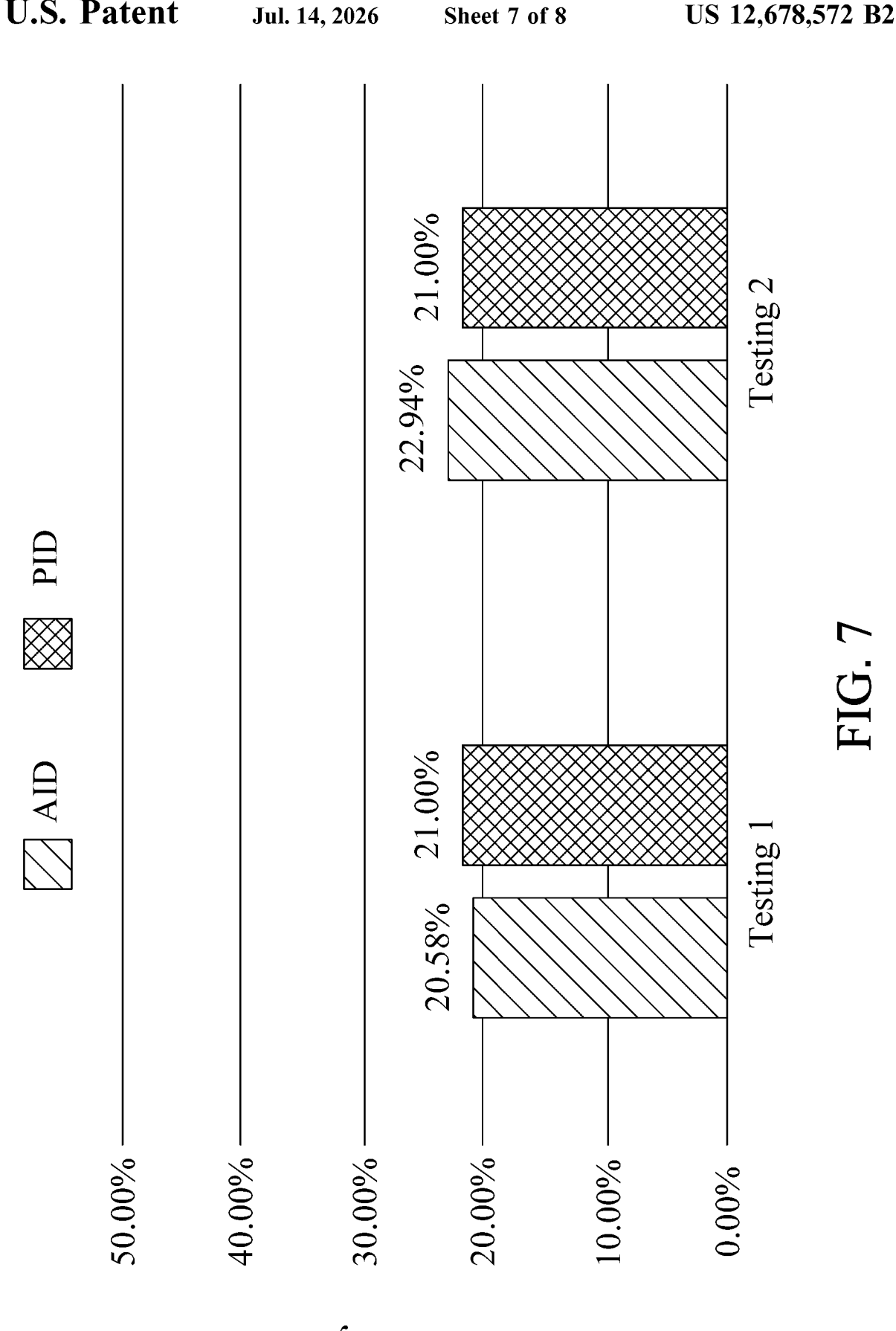
FIG. 7 is a bar chart showing another comparison of the PIDs and the AIDs of two tests for two different persons.

FIG. 7 shows the comparisons of the PIDs and the AIDs after two testing. As shown in FIG. 6, the PID of the testing 1 is similar to the patient's AID of the testing 1, and the PID of the testing 2 is similar to the AID of the testing 2.

Use Case

Figure 8:
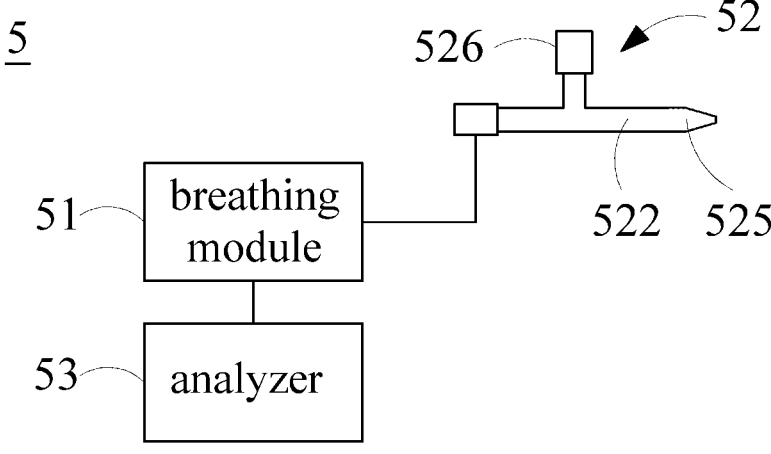
FIG. 8 is a schematic diagram showing another system for estimating the inhale dose of a person according to an embodiment of the disclosure.

FIG. 8 shows another system 5, including the breathing module 51, an apparatus 52 and an analyzer 53. The system 5 is the same to the system 1 shown in FIG. 1 except that no filter for measuring the actual inhale dose is attached between the inlet path 522 and the patient port 525 of the inhaler 52.

After the system 5 is set up, the operator first inputs the type of the apparatus 52. The analyzer 53 obtains the parameters DP and RP from a lookup table according to the inhaler type input by the operator. Then, the operator turns on the nebulizer 526 and asks a patient C to start using the patient port 525 of the apparatus 52 to breath. The breathing module 51 then starts measuring the parameters of the breath pattern of the patient C in real time and outputs those parameters to the analyzer 53.

After a predetermined period, the analyzer 53 calculates a PID of the patient C. The PID may be shown to a doctor for his or her reference. The doctor may adjust the flow rate of the nebulizer 526 based on the PID in real time to deliver the drug in aerosol form to the patient C more effectively.

The present disclosure has been described with some preferred embodiments thereof and it is understood that the preferred embodiments are only illustrative and not intended to limit the present invention in any way and many changes and modifications in the described embodiments can be carried out without departing from the scope and the spirit of the invention that is intended to be limited only by the appended claims.

What is claimed is:

1. A method for estimating an inhale dose when a drug is delivered to a person using an inhaler, the method comprising:

obtaining, by an analyzer from a breathing module, a first-type parameter related to a breath pattern of the person when the drug is delivered to the person through the inhaler;

obtaining, by the analyzer, a second-type parameter related to the inhaler;

estimating, by the analyzer, a predicted inhale dose of the drug after the drug is delivered to the person through the inhaler for a period of time, based on the first-type parameter and the second-type parameter; and showing the predicted inhale dose upon the predicted inhale dose being estimated by the analyzer, wherein the predicted inhale dose is estimated according to the following formula:

$$PID=(TD-RC)*(I/(E+I))-DP+RP$$

wherein TD is a total drug amount in an aerosol generator of the inhaler and obtained from the aerosol generator, RC is a drug residue amount in the aerosol generator and obtained from the aerosol generator, I is an inspiratory time of the person and derived from the breath pattern, E is an expiratory time of the person and derived from the breath pattern, DP is a drug deposit in an inlet path of the inhaler and included in the second-type parameter, and RP is a drug reserve in an outlet path of the inhaler and included in the second-type parameter.

2. The method of claim 1, wherein the first-type parameter includes an inspiratory time of the person or an expiratory time of the person.

3. The method of claim 1, wherein the first-type parameter is obtained by measuring the breath pattern of the person.

4. The method of claim 1, wherein the second-type parameter is obtained from a look-up table according to a type of the inhaler.

5. An apparatus for estimating an inhale dose when a drug is delivered to a person using an inhaler, the apparatus comprising:

a processor; and a memory storing instructions thereon, wherein the processor is capable of executing the instructions to perform the steps of:

obtaining, from a breathing module, a first-type parameter related to a breath pattern of the person when the drug is delivered to the person through the inhaler;

obtaining a second-type parameter related to the inhaler;

estimating a predicted inhale dose of the drug after the drug is delivered to the person through the inhaler for a period of time, based on the first-type parameter and the second-type parameter; and showing the predicted inhale dose upon the predicted inhale dose being estimated by the analyzer, wherein the predicted inhale dose is estimated according to the following formula:

$$PID=(TD-RC)*(I/(E+I))-DP+RP$$

wherein TD is a total drug amount in an aerosol generator of the inhaler and is obtained from the aerosol generator, RC is a drug residue amount in the aerosol generator and is obtained from the aerosol generator, I is an inspiratory time of the person and is derived from the breath pattern, E is an expiratory time of the person and is derived from the breath pattern, DP is a drug deposit in an inlet path of the inhaler and is included in the second-type parameter, and RP is a drug reserve in an outlet path of the inhaler and is included in the second-type parameter.

6. The apparatus of claim 5, wherein the first-type parameter includes an inspiratory time of the person or an expiratory time of the person.

7. The apparatus of claim 5, wherein the first-type parameter is obtained by measuring the breath pattern of the person.

8. The apparatus of claim 5, wherein the second-type parameter is obtained from a look-up table according to a type of the inhaler.

9. A non-transitory storage medium with instructions stored thereon for estimating an inhale dose when a drug is delivered to a person using an inhaler, wherein a processor is capable of executing the instructions to perform the following steps:

obtaining, by an analyzer from a breathing module, a first-type parameter related to a breath pattern of the person when the drug is delivered to the person through the inhaler;

obtaining, by the analyzer, a second-type parameter related to the inhaler;

estimating, by the analyzer, a predicted inhale dose of the drug after the drug is delivered to the person through the inhaler for a period of time, based on the first-type parameter and the second-type parameter; and showing the predicted inhale dose upon the predicted inhale dose being estimated by the analyzer, wherein the predicted inhale dose is estimated according to the following formula:

$$PID=(TD-RC)*(I/(E+I))-DP+RP$$

wherein TD is a total drug amount in an aerosol generator of the inhaler and is obtained from the aerosol generator, RC is a drug residue amount in the aerosol generator and is obtained from the aerosol generator, I is an inspiratory time of the person and is derived from the breath pattern, E is an expiratory time of the person and is derived from the breath pattern, DP is a drug deposit in an inlet path of the inhaler and is included in the second-type parameter, and RP is a drug reserve in an outlet path of the inhaler and is included in the second-type parameter.

10. The non-transitory storage medium of claim 9, wherein the first-type parameter includes an inspiratory time of the person or an expiratory time of the person.

11. The non-transitory storage medium of claim 9, wherein the first-type parameter is obtained by measuring the breath pattern of the person.

12. The non-transitory storage medium of claim 9, wherein the second- type parameter is obtained from a look-up table according to a type of the inhaler.

13. A method for delivering a drug to a person using an inhaler, comprising:

inputting, to an analyzer, information related to a type of the inhaler;

measuring, by a breathing module, a breath pattern of the person; and determining an inhale dose according to a predicted inhale dose of the drug shown by the analyzer after the drug is delivered to the person through the inhaler for a period of time, wherein the predicted inhale dose of the drug is estimated by the analyzer based on a first-type parameter related to the breath pattern of the person and a second-type parameter related to the inhaler, wherein the predicted inhale dose is estimated according to the following formula:

$$PID=(TD-RC)*(I/(E+I))-DP+RP$$

wherein TD is a total drug amount in an aerosol generator of the inhaler and is obtained from the aerosol generator, RC is a drug residue amount in the aerosol generator and is obtained from the aerosol generator, I is an inspiratory time of the person and is derived from the breath pattern, E is an expiratory time of the person and is derived from the breath pattern, DP is a drug deposit in an inlet path of the inhaler and is included in the second-type parameter, and RP is a drug reserve in an outlet path of the inhaler and is included in the second-type parameter.

14. The method of claim 13, wherein the first-type parameter includes an inspiratory time of the person or an expiratory time of the person.

15. The method of claim 13, wherein the second-type parameter is obtained from a look-up table according to the type of the inhaler.

\* \* \* \* \*